United States Patent [19]

Anzai et al.

[11] Patent Number: 5,368,971
[45] Date of Patent: Nov. 29, 1994

[54] ELECTROPHOTOGRAPHIC TONER CONTAINING A ZINC BENZOATE COMPOUND

[75] Inventors: Mitsutoshi Anzai, Ushiku; Noboru Akuzawa, Kita; Yuuji Matsuura, Tsukuba; Genpei Sugiyama, Kita, all of Japan

[73] Assignee: Hodogaya Chemical Co., Ltd., Tokyo, Japan

[21] Appl. No.: 104,601

[22] Filed: Aug. 11, 1993

Related U.S. Application Data

[63] Continuation of Ser. No. 988,026, Dec. 9, 1992, abandoned, which is a continuation of Ser. No. 709,962, Jun. 4, 1991, abandoned.

[30] Foreign Application Priority Data

Jun. 29, 1990 [JP] Japan .................. 2-169757
Mar. 8, 1991 [JP] Japan .................. 3-042164

[51] Int. Cl.$^5$ .................................. G03G 9/097
[52] U.S. Cl. ............................ 430/110; 430/109
[58] Field of Search ........................... 430/110, 109

[56] References Cited

U.S. PATENT DOCUMENTS 1,933,520 10/1933 Broson .................. 134/57
4,762,763 8/1988 Nomura et al. .......... 430/110
4,888,263 12/1989 Tomita et al. ........... 430/106

*Primary Examiner*—Marion E. McCamish
*Assistant Examiner*—Rosemary Ashton
*Attorney, Agent, or Firm*—Wenderoth, Lind & Ponack

[57] ABSTRACT

A zinc benzoate compound represented by the following general formula:

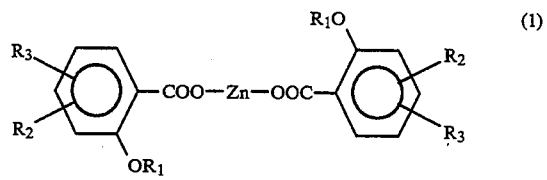

wherein $R_1$ represents an alkyl or aralkyl group; and $R_2$ and $R_3$, independently from each other, each represent an alkyl, aralkyl, aryl, alkoxy or acyl group, an amino group which may be substituted, a nitro group or a halogen atom. The compound of the general formula (1) is colorless, highly stable and has excellent dispersibility in a binder resin for an electrophotographic toner, and can impart excellent frictional electrification properties to a toner, therefore being useful particularly as a charge control agent for an electrophotographic toner.

1 Claim, No Drawings

ELECTROPHOTOGRAPHIC TONER CONTAINING A ZINC BENZOATE COMPOUND

This application is a continuation of now abandoned application, Ser. No. 07/988,026, filed Dec. 9, 1992, which is a continuation of now abandoned application, Ser. No. 07/709,962, filed Jun. 4, 1991.

FIELD OF THE INVENTION

The present invention relates to a compound useful as a charge control agent of an electrophotographic toner which is used for developing an electrostatic latent image formed in electrophotography, electrostatic recording or the like, and an electrophotographic toner containing the same.

BACKGROUND OF THE INVENTION

In the image-forming process according to electrophotography, an electrostatic latent image is formed on an inorganic photosensitive material of selenium, a selenium alloy, cadmium sulfide or amorphous silicon, or on an organic photosensitive material comprising a charge generating material and a charge transporting material, developed with a toner, transferred and fixed to a paper sheet or a plastic film to give a visual image thereon. The photosensitive material is chargeable positively or negatively depending upon the constitution thereof. In a case wherein an image area remains as an electrostatic latent image after the exposure to light, a toner which is chargeable with a polarity reverse to that of the photosensitive material is used in the development of the latent image, while in a case wherein the charge in an image area is erased to conduct reversal development, a toner which is chargeable with the same polarity as that of the photosensitive material is used in the development of the latent image.

Although a toner is substantially constituted of a binder resin, a coloring material and additives, a charge control agent is generally also added to the toner in order to impart desirable frictional electrification properties (charge rate, charge level or charge stability), long-term stability and environmental stability thereto. The characteristics of the toner are greatly affected by the charge control agent. In a case wherein the development is conducted with a positively chargeable photosensitive material and a negatively chargeable toner, or in a case wherein the reversal development is conducted with a negatively chargeable photosensitive material, a negatively chargeable toner is used and a negatively chargeable charge control agent is incorporated thereinto.

Further, the charge control agent to be used for a color toner must be colored so lightly as not to exert any influence on the color of the toner, and preferably is colorless. Such a light-colored or colorless charge control agent includes metal complex salts of hydroxybenzoic acid derivatives as described in Japanese Examined Patent Publication No. 42752/1980 and Japanese Unexamined Patent Publication Nos. 69073/1986 and 221756/1986; metal salts of aromatic dicarboxylic acids as described in Japan Unexamined Patent Publication No. 111541/1982; metal complex salts of anthranilic acid derivatives as described in Japanese Unexamined Patent Publication Nos. 141453/1986 and 94856/1987; organoboron compounds as described in U.S. Pat. No. 4767688 and Japanese Unexamined Patent Publication No. 306861/1989; and biphenol compounds as described in Japanese Unexamined Patent Publication No. 3149/1986.

However, some of these charge control agents are chromium compounds which are in danger of causing environmental pollution, some of them are unavailable as completely colorless ones' and some of them each have a disadvantage of a low charge imparting effect, generating a large amount of a reversely charged toner, poor dispersibility or poor stability. Thus, no charge control agent exhibiting satisfactory performances has been found as yet.

SUMMARY OF THE INVENTION

An object of the present invention is therefore to provide a colorless stable compound which is useful as a charge control agent of an electrophotographic toner.

Another object of the present invention is to provide an electrophotographic toner containing the above-described compound as a charge control agent which has excellent dispersibility in a binder resin.

Further object of the present invention is to provide an electrophotographic toner which has excellent frictional electrification properties and can constantly give a stable, high-quality image.

The inventors of the present invention have found a colorless stable compound which has excellent dispersibility in a binder resin for an electrophotographic toner and can impart excellent frictional electrification properties to a toner. The inventors have also found that an excellent electrophotographic toner can be obtained by using this compound as a charge control agent. The present invention has been accomplished on the basis of these findings.

According to the present invention, there is provided a zinc benzoate compound represented by the following general formula:

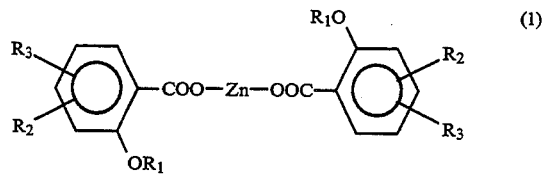

wherein $R_1$ represents an alkyl or aralkyl group; and $R_2$ and $R_3$, independently from each other, each represent an alkyl, aralkyl, aryl, alkoxy or acyl group, an amino group which may be substituted, a nitro or a halogen atom.

Further, an electrophotographic toner according to the present invention is characterized by containing the zinc benzoate compound represented by the above-described general formula (1) as a charge control agent.

PREFERRED EMBODIMENTS OF THE INVENTION

The electrophotographic toner of the present invention is substantially constituted of a binder resin, a coloring material and the zinc benzoate compound represented by the general formula (1) as a charge control agent. The process for preparing the electrophotographic toner includes one which comprises kneading a mixture of these components in a heat mixing apparatus while keeping the binder resin in a molten state, cooling the resulting mixture and crushing, pulverizing and classifying it; one which comprises dissolving a mixture of these components in a solvent, spraying the resulting solution to conduct the formation of fine particles and drying and classifying the particles; and one which comprises adding a coloring material and the compound represented by the general formula (1) to a dispersion of the monomers and polymerizing the resulting dispersion.

The binder resin includes polystyrene, styrene-methacrylate copolymer, styrene-propylene copolymer, styrene-butadiene copolymer, acrylic resin, styrene-maleic acid copolymer, olefin resin, polyester, epoxy resin, polyurethane resin and polyvinyl butyral, which may be used alone or as a mixture of two or more of them.

As a coloring material, carbon black is generally used for black toners and conventionally known coloring materials which will be described below are also used for color toners. The yellow coloring material to be used in the present invention includes organic azo pigments such as C.I. Pigment Yellow 1, C.I. Pigment Yellow 5, C.I. Pigment Yellow 12 and C.I. Pigment Yellow 17; inorganic pigments such as yellow ocher; and oil-soluble dyes such as C.I. Solvent Yellow 2, C.I. Solvent Yellow 6, C.I. Solvent Yellow 14 and C.I. Solvent Yellow 19. The magenta colorant to be used includes azo pigments such as C.I. Pigment Red 57 and C.I. Pigment Red 57:1; xanthene pigments such as C.I. Pigment Violet 1 and C.I. Pigment Red 81; thioindigo pigments such as C.I. Pigment Red 87, C.I. Vat Red 1 and C.I. Pigment Violet 38; and oil-soluble dyes such as C.I. Solvent Red 19, C.I. Solvent Red 49 and C.I. Solvent Red 52. The cyan colorant to be used includes triphenylmethane pigments such as C.I. Pigment Blue 1; phthalocyanine pigments such as C.I. Pigment Blue 15 and C.I. Pigment Blue 17; and oil-soluble dyes such as C.I. Solvent blue 25, C.I. Solvent Blue 40 and C.I. Solvent Blue 70.

The zinc benzoate compound of the general formula (1) to be used as a charge control agent in the present invention includes zinc 5-methyl-2-ethoxybenzoate, zinc 5-t-butyl-2-methoxybenzoate, zinc 3,5-dimethyl-2-methoxybenzoate, zinc 3,5-diisopropyl-2-methoxybenzoate, zinc 3,5-di-t-butyl-2-methoxybenzoate, zinc 3,5-di-t-butyl-2-ethoxybenzoate, zinc 3,5-diisopropyl-2-propoxybenzoate, zinc 3-methyl-5-t-butyl-2-methoxybenzoate, zinc 3,5-dibenzyl-2-methoxybenzoate, zinc 3,5-di-α-methylbenzyl-2-methoxybenzoate, zinc 3,5-dimethyl-2-benzyloxybenzoate, zinc 3,5-di-t-amyl-2-butyloxybenzoate, zinc 3-methyl-5-phenyl-2-methoxybenzoate, zinc 2,3-dimethoxybenzoate, zinc 2,5-dimethoxybenzoate, zinc 5-methoxy-2-ethoxybenzoate, zinc 5-acetyl-2-methoxybenzoate, zinc 4-diethylamino-2-ethoxybenzoate, zinc 5-dibutylamino-2-butoxybenzoate, zinc 5-nitro-2-methoxybenzoate and zinc 4-chloro-2-ethoxybenzoate.

A general process for the preparation of the zinc benzoate compound according to the present invention is as follows. That is, a benzoic acid derivative represented by the following general formula:

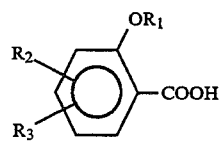

(wherein $R_1$, $R_2$ and $R_3$ are each as defined with respect to the above general formula (1)) is added to water and/or a water-soluble organic solvent. An alkali salt such as caustic soda or caustic potash is added to the resulting mixture to dissolve the derivative in the water and/or water-soluble solvent. Into the resulting solution is added an aqueous solution of a water-soluble zinc salt such as zinc sulfate. The obtained solution is reacted at a room temperature or an elevated temperature of up to about 80° C. for several hours and cooled by allowing to stand to precipitate a white crystal. This crystal is recovered by filtration, washed with water and dried to give a zinc benzoate compound represented by the general formula (1).

If necessary, the toner of the present invention may further contain other additives with the purpose of protection of a photosensitive material and a carrier, improvement of the fluidity of the toner, control of the thermal, electrical or physical characteristics of the toner, control of the resistance or softening point of the toner and/or improvement of the fixability thereof. Such additives include hydrophobic silica, metal soap, fluorocarbon surfactant, dioctyl phthalate, wax, tin oxide and electrically conductive zinc oxide.

When the toner of the present invention is used as a dual-component developer, the carrier to be used together with the toner includes fine glass beads, powdered iron, powdered ferrite, binder-type carriers comprising a resin particle containing a magnetic material dispersed therein and carriers coated with a resin such as polyester, fluorocarbon, acrylic or silicone resin. Further, the compound of the general formula (1) and the toner containing the compound also exhibit excellent performances when used as a mono-component developer.

The present invention will now be described in more detail by referring to the following Preparative Examples with respect to the compounds of the present invention and Examples with respect to the toners of the present invention, wherein all parts represent parts by weight.

Preparative Example 1 zinc 3,5-di-t-butyl-2-methoxybenzoate (compound No. 1)

Five parts of 3,5-di-t-butyl-2-methoxybenzoic acid was added to 48 parts of water, followed by the dropwise addition of an aqueous solution of 1.2 parts of 96% potassium hydroxide in 2 parts of water. The resulting mixture was converted into a solution by heating to a temperature of 40° to 50° C. An aqueous solution of 2.7 parts of zinc sulfate heptahydrate in 10 parts of water was dropped into the solution at 60° C. over a period of 15 minutes. After the completion of the dropping, the obtained mixture was stirred at that temperature for 2 hours, cooled to a room temperature and filtered to recover a white crystalline precipitate. This precipitate was dispersed in 60 parts of water, washed therewith and filtered. The filter cake was dried to give 3.8 parts of a white crystal. The melting point thereof was 263° to 265° C.

The infrared absorption spectroscopic analysis of this zinc salt compound revealed the disappearance of the absorption at 1680 cm$^{-1}$ assignable to the stretching vibration of a carbonyl group, by which the conversion of 3,5-di-t-butyl-2-methoxybenzoic acid into its zinc salt was ascertained (Instrument: infrared spectrophotometer type IR-700 mfd. by Nippon Bunko Kogyo K.K., Method: KBr tablet method). The results of the elemental analysis of the salt are as follows:

|  | carbon (%) | hydrogen (%) | zinc (%) |
| --- | --- | --- | --- |
| calculated | 64.91 | 7.83 | 11.04 |
| found | 64.73 | 7.99 | 11.51 |

Preparative Example 2 zinc 3,5-diisopropyl-2-methoxybenzoate (compound No. 2)

Five parts of 3,5-diisopropyl-2-methoxybenzoic acid was dissolved in 80 parts of methyl alcohol, followed by the addition of an aqueous solution of 1.3 parts of 96% potassium hydroxide in 10 parts of water. The resulting mixture was heated to 60° C. An aqueous solution of 3.2 parts of zinc sulfate heptahydrate in 10 parts of water was dropped into the resulting mixture over a period of 15 minutes. After the completion of the dropping, the obtained mixture was stirred at that temperature for 2 hours, cooled to a room temperature and filtered to recover a white crystalline precipitate. This precipitate was dispersed in 60 parts of water, washed therewith and filtered. The obtained filter cake was dried to give 4.8 parts of a white crystal. The melting point thereof was 104 to 107° C.

The infrared absorption spectroscopic analysis of this zinc salt compound in a similar manner to that of Preparative Example 1 revealed the disappearance of the absorption at 1690 cm$^{-1}$ assignable to the stretching vibration of a carbonyl group, by which the conversion of 3,5-diisopropyl-2-methoxybenzoic acid into its zinc salt was ascertained.

The results of the elemental analysis of the salt are as follows:

|  | carbon (%) | hydrogen (%) | zinc (%) |
| --- | --- | --- | --- |
| calculated | 62.74 | 7.15 | 12.20 |
| found | 62.53 | 7.36 | 12.61 |

Preparative Example 3 zinc 3,5-di-t-butyl-2-ethoxybenzoate (compound No. 3)

Five parts of 3,5-di-t-butyl-2-ethoxybenzoic acid was dissolved in 80 parts of methyl alcohol, followed by the addition of an aqueous solution of 1.1 parts of 96% potassium hydroxide in 10 parts of water. The resulting mixture was heated to 60° C. An aqueous solution of 2.6 parts of zinc sulfate heptahydrate in 10 parts of water was dropped into the resulting mixture over a period of 15 minutes. After the completion of the dropping, the obtained mixture was stirred at that temperature for 2 hours, cooled to a room temperature and filtered to recover a white crystalline precipitate. This precipitate was dispersed in 60 parts of water, washed therewith and filtered. The filter cake was dried to give 3.9 parts of a white crystal. The melting point thereof was 178° to 180° C.

The infrared absorption spectroscopic analysis of this zinc salt compound in a similar manner to that of Preparative Example 1 revealed the disappearance of the absorption at 1690 cm$^{-1}$ assignable to the stretching vibration of a carbonyl group, by which the conversion of 3,5-di-t-butyl-2-ethoxybenzoic acid into its zinc salt was ascertained.

The results of the elemental analysis of the salt are as follows:

|  | carbon (%) | hydrogen (%) | zinc (%) |
| --- | --- | --- | --- |
| calculated | 65.85 | 8.13 | 10.54 |
| found | 65.57 | 8.29 | 10.87 |

The following compounds were each prepared in a similar manner to that described above.

Preparative Example 4: (Compound No. 4)

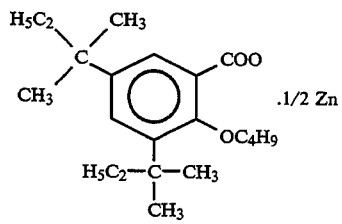

Preparative Example 5: (Compound No. 5)

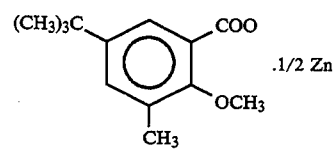

Preparative Example 6: (Compound No. 6)

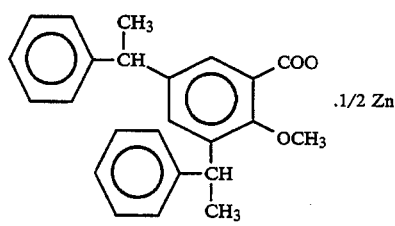

Preparative Example 7: (Compound No. 7)

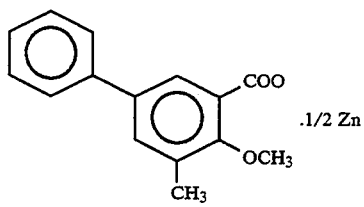

Preparative Example 8: (Compound No. 8)

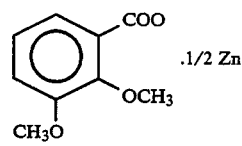

Preparative Example 9: (Compound No. 9)

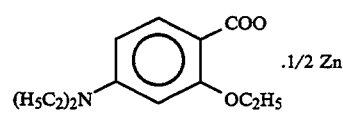

Preparative Example 10: (Compound No. 10)

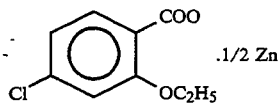

EXAMPLE 1

One part of zinc 3,5-di-t-butyl-2-methoxybenzoate (compound No. 1), 5 parts of carbon black and 94 parts of a styrene-ethylhexyl methacrylate copolymer were kneaded together in a heat mixing apparatus. The resulting mixture was cooled, roughly pulverized with a hammer mill, milled with a jet mill, and classified to give a black toner having a size of 10 to 12 $\mu$m. This toner was mixed with an iron powder carrier at a weight ratio of 4:100. When the obtained mixture was shaken, the toner was charged negatively. The triboelectric charge of the toner was $-35$ $\mu$C/g as determined with a blow-off type instrument for the measurement of powder charge. The above mixture was applied to a remodeled commercially available copying machine to conduct printing. Clear images were obtained in the beginning and even after repeating the copying ten thousand times.

EXAMPLE 2

One part of zinc 3,5-diisopropyl-2-methoxybenzoate (compound No. 2), 5 parts of carbon black and 94 parts of a styrene-ethylhexyl methacrylate copolymer were kneaded together in a heat mixing apparatus. The resulting mixture was cooled, roughly pulverized with a hammer mill, milled with a jet mill, and classified to give a black toner having a size of 10 to 12 $\mu$m. This toner was mixed with an iron powder carrier at a weight ratio of 4:100. When the obtained mixture was shaken, the toner was charged negatively. The triboelectric charge of the toner was $-30$ $\mu$C/g as determined with a blow-off type instrument for the measurement of powder charge. The above mixture was applied to a remodeled commercially available copying machine to conduct printing. Clear images were obtained in the beginning and even after repeating the copying ten thousand times.

EXAMPLE 3

One part of zinc 3,5-di-t-butyl-2-methoxybenzoate (compound No. 1), 5 parts of SPIRON (registered trade mark) R BLUE 2BNH which is an oil-soluble copper phthalocyanine dye, and 94 parts of a styrene-butyl methacrylate copolymer were kneaded together in a heat mixing apparatus. The resulting mixture was cooled, roughly pulverized with a hammer mill, milled with a jet mill, and classified to give a blue toner having a size of 10 to 12 $\mu$m. This toner was mixed with an iron powder carrier at a weight ratio of 4:100. When the obtained mixture was shaken, the toner was charged negatively. The triboelectric charge of the toner was $-37$ $\mu$C/g as determined with a blow-off type instrument for the measurement of powder charge. The above mixture was applied to a remodeled commercially available copying machine to conduct printing. Clear images were obtained in the beginning and even after repeating the copying ten thousand times.

EXAMPLE 4

One part of zinc 3,5-di-t-butyl-2-ethoxybenzoate (compound No. 3), 5 parts of carbon black and 94 parts of a styrene-ethylhexyl methacrylate copolymer were kneaded together in a heat mixing apparatus. The resulting mixture was cooled, roughly pulverized with a hammer mill, milled with a jet mill, and classified to give black toner having a size of 10 to 12 $\mu$m. This toner was mixed with a silicone resin-coated carrier at a weight ratio of 4:100. When the obtained mixture was shaken, the toner was charged negatively. The triboelectric charge of the toner was $-18$ $\mu$C/g as determined with a blow-off type instrument for the measurement of powder charge. The above mixture was applied to a remodeled commercially available copying machine to conduct printing. Clear images were obtained in the beginning and even after repeating the copying ten thousand times.

EXAMPLES 5 to 12

The same procedure as that of Example 1 was repeated except that each of the zinc salt compounds listed in Table 1 was used instead of the zinc 3,5-di-t-butyl-2-methoxybenzoate. The results given in Table 1 were obtained.

TABLE 1

| Example | Compound No. | Triboelectric charge of toner ($-\mu$C/g) | State of printed image in the beginning | State of printed image after repeating the printing 10,000 times |
| --- | --- | --- | --- | --- |
| 5 | 3 | 32 | clear | clear |
| 6 | 4 | 28 | clear | clear |
| 7 | 5 | 33 | clear | clear |
| 8 | 6 | 35 | clear | clear |
| 9 | 7 | 26 | clear | clear |
| 10 | 8 | 30 | clear | clear |
| 11 | 9 | 22 | clear | clear |
| 12 | 10 | 38 | clear | clear |

The zinc benzoate compound of the present invention is colorless, highly stable, and has excellent dispersibility in a binder resin for an electrophotographic toner, and can impart excellent frictional electrification properties to a toner, therefore being useful particularly as a charge control agent for an electrophotographic toner.

An electrophotographic toner containing the above compound as a charge control agent can constantly give high-quality images repeatedly.

What is claimed is:

1. An electrophotographic developer comprising a binder resin, a coloring material, a carrier and a charge control agent, said charge control agent being a zinc benzoate compound represented by the following general formula:

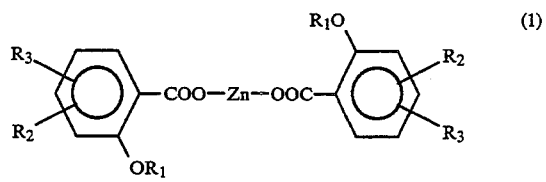

wherein $R_1$ represents an alkyl group; and $R_2$ and $R_3$, independently from each other, each represent an alkyl, aralkyl, aryl or alkoxy group.

* * * * *